(12) United States Patent
Haas

(10) Patent No.: US 7,745,227 B2
(45) Date of Patent: Jun. 29, 2010

(54) SYSTEM FOR ANALYSIS OF EXPLOSIVES

(75) Inventor: Jeffrey S. Haas, San Ramon, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 1725 days.

(21) Appl. No.: 10/915,973

(22) Filed: Aug. 11, 2004

(65) Prior Publication Data

US 2005/0064601 A1 Mar. 24, 2005

Related U.S. Application Data

(60) Provisional application No. 60/494,870, filed on Aug. 12, 2003.

(51) Int. Cl.
G01N 30/90 (2006.01)
G01N 33/22 (2006.01)

(52) U.S. Cl. ...................... 436/162; 436/110
(58) Field of Classification Search .................. 436/162
See application file for complete search history.

(56) References Cited

U.S. PATENT DOCUMENTS

| 4,554,133 | A | | 11/1985 | Leichnitz |
| 4,783,316 | A | | 11/1988 | Pannwitz |
| 4,788,039 | A | * | 11/1988 | Glattstein ..................... 422/61 |
| 5,310,681 | A | | 5/1994 | Rounbehler et al. |
| 5,551,278 | A | | 9/1996 | Rounbehler et al. |
| 5,638,166 | A | | 6/1997 | Funsten et al. |
| 5,679,584 | A | | 10/1997 | Mileaf et al. |
| 5,912,466 | A | | 6/1999 | Funsten et al. |
| 6,096,205 | A | | 8/2000 | Haas et al. |
| 6,245,576 | B1 | | 6/2001 | Hiley |
| 6,406,918 | B1 | | 6/2002 | Bannister et al. |
| 6,454,939 | B1 | | 9/2002 | Haas et al. |
| 6,470,730 | B1 | | 10/2002 | Chamberlain |
| 6,477,907 | B1 | | 11/2002 | Chambers et al. |

OTHER PUBLICATIONS

Haas, J.,Klunder, G., Whipple, R. and Andresen, B. "Thin-Layer Chromatography (TLC) Analysis of Exhumed MMR Ordnance" Sep. 1998 . Lawrence Livermore National Laboratory Forensic Science Center, pp. 1-9.*

Sae-Im Nam, "On-site analysis of explosives in soil. Evaluation of thin-layer chromatography for confirmation of analyte identity" Aug. 1997 U.S. Army Corps of Engineers Special Report 97-21, pp. i-14.*

(Continued)

*Primary Examiner*—Jill Warden
*Assistant Examiner*—Timothy G Kingan
(74) *Attorney, Agent, or Firm*—Eddie E. Scott; John H. Lee

(57) ABSTRACT

A system for analysis of explosives. Samples are spotted on a thin layer chromatography plate. Multi-component explosives standards are spotted on the thin layer chromatography plate. The thin layer chromatography plate is dipped in a solvent mixture and chromatography is allowed to proceed. The thin layer chromatography plate is dipped in reagent 1. The thin layer chromatography plate is heated. The thin layer chromatography plate is dipped in reagent 2.

2 Claims, 4 Drawing Sheets

OTHER PUBLICATIONS

Simion Gocan, "Mobile Phases in Thin-Layer Chromatography" in Modern Thin-Layer Chromatography (ed. Nelu Grinberg) 1990, Marcel Dekker, Inc. New York and Basel pp. 139-172.*

J.B. Lloyd, "Detection of microgram amounts of nitroglycerin and related compounds". 1967, J. of the Forensic Science Society 7(4): 198.*

Yinon, J., et al., "The Analysis of Explosives," Pergamon Press, 1981, 73 pages.

Parker, R.G., et al., "Analysis of Explosives and Explosive Residues. Part 1: Chemical Tests," Journal of Forensic Sciences, vol. 20, No. 1, 1975, pp. 133-140.

Grant, P., "Chemistry Field Assets Instruments & Otherwise," Iraq Planning Meeting, Albuquerque, NM, Lawrence Livermore National Laboratory Forensic Science Center, Aug. 2002, 4 pages.

Thornton, J.I., "The Chemistry of Death by Gunshot," Analytica Chimica Acta 288 (1994) Elseiver Science B.V., pp. 71-81.

Jenkins, T., et al., "Development of Field Screening Methods for TNT, 2,4-DNT and RDX in Soil," Geological Sci., Talonia, vol. 39, No. 4, pp. 419-428, Pergamon Press, 1992.

Crockett, A.B., et al., "Field Sampling and Selecting On-Site Analytical Methods for Explosives in Soil," EPA Federal Facilities Forum Issue, EPA/540/R-97/501, Nov. 1996, pp. 1-33.

Crockett, A.B., et al., Field Sampling and Selecting On-Site Analytical Methods for Explosives in Soil, EPA Project Summary, EPA/540/S-97/501, Dec. 1996, pp. 1-9.

Mamginnell, R. P., et al., Finite Element Modeling of a Microphotplate for Microfluidic Applications, Presented at MEMs99, Sandia National Laboratories, Harvard Thermal Inc., 1999, 6 pages.

Beveridge, A., "Forensic Investigation of Explosions," Taylor & Francis, Defense Research Agency, Farnborough, Hants GU14 6TD UK, 1993, 13 pages.

Meng, H., et al., "Gunshot Residue Analysis—A Review," Journal of Forensic Sciences, 42(4), 1997, pp. 557-570.

Hiley, R., "Investigations of Thin Layer Chromatographic Techniques Used for Forensic Explosives Analysis in the Early 1970s," Hiley-TLC Techniques for Explosives Analysis, Journal of Forensic Sciences, Jul. 1993, pp. 864-873.

Fox, J. B., Jr., "Kinetics and Mechanisms of the Griess Reaction," Analytical Chemistry, vol. 51, No. 9, Aug. 1979, 14 pages.

Nam, S., et al., "On-Site Analysis of Explosives in Soil: Evaluation of Thin-Layer Chromatography for Confirmation of Analyte Identity," U.S. Army Environmental Center, Aberdeen Proving Ground, MD, 2000, 4 pages.

Nam, S., "On-Site Analysis of Explosives in Soil: Evaluation of Thin-Layer Chromatography for Confirmation of Analyte Identiy," U.S. Army Envionmental Center, U.S. Army Corps of Engineers, Special Report 97-21, Aug. 1997, 20 pages.

Jenkins, T. F., et al., "On-Site Analysis for High Concentrations of Explosives in Soil Extraction Kinetics and Dilution Procedures," U.S. Army Environmental Center, U.S. Army Corps of Engieers, Special Report 96-10, May 1996, 18 pages.

Fetterolf, D., "Portable Instrumentation: New Weapons in the War Against Drugs and Terrorism," SPIE, vol. 2092, 1993, pp. 40-52.

Krishnamurthy, R., et al., "Simultaneous Detection of High Explosives in Post-Explosion Debris by HPTLC with Two Successive Mobile Phases," Journal of Planar Chromatography, vol. 12, Sep./Oct. 1999, pp. 394-397.

Twibell, J., et al., "The Persistence of Military Explosives on Hands," Journal of Forensic Sciences, vol. 29, No. 1, Jan. 1984, pp. 284-290.

Peak, S.A.., "A Thin-Layer Chromatographic Procedure for Confirming the Presence and Identity of Smokeless Powder Flakes," Journal of Forensic Sciences, vol. 25, No. 3, Jul. 1980, pp. 679-681.

Haas, J., et al., "Thin-Layer Chromatographic (TLC) Analysis of Exhumed MMR Ordnance," Lawrence Livermore National Laboratory Forensic Science Center, Sep. 1998, 9 pages.

Douse, J.M.F., et al., "Trace Analysis of Explosives and Firearm Discharge Residues in the Metropolitan Police Forensic Science Laboratory," Metropolitan Police Forensic Science Laboratory, London, UK, Journal of Energetic Materials, vol. 4, 1986, pp. 169-188.

Twibell, J., et al., "Transfer of Nitroglycerine to Hands During Contact with Commercial Explosives," Journal of Forensic Sciences, vol. 27, No. 4, Oct. 1982, pp. 783-791.

Andresen, B., et al., "Recent Innovations for the Detection of Propellant Stablizers and HE in the Field," 2000 Global Demilitarization Symposium & Exhibition, National Defense Industrial Association, Event #058, Coeur d'Alene, ID, May 2000, 20 pages.

* cited by examiner

SYSTEM FOR ANALYSIS OF EXPLOSIVES

CROSS-REFERENCE TO RELATED APPLICATIONS

This application claims the benefit of U.S. Provisional Patent Application No. 60/494,870 filed Aug. 12, 2003 and titled "Unique Methodology for the Analysis of Explosives." U.S. Provisional Patent Application No. 60/494,870 filed Aug. 12, 2003 and titled "Unique Methodology for the Analysis of Explosives" is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to testing and analysis and more particularly to a system for analysis of explosives.

2. State of Technology

U.S. Pat. No. 6,096,205 for a hand portable thin-layer chromatography system issued Apr. 1, 2000 to Jeffrey S. Haas, Fredrick R. Kelly, John F. Bushman, Michael H. Wiefel, and Wayne A. Jensen provides the following state of the art information: "Various analytical techniques are used to measure the type and amount of contamination from unknown chemicals in environmental, industrial, civilian, and military situations. Conventional thin-layer chromatography (TLC) analysis is routinely used in analytical laboratories worldwide for quantitative and qualitative characterization of unknowns. This technique is ideal for rapid pre-screening and identification of known and unknown chemicals. TLC allows multiple samples and standards (in mg to ng quantities) to be chromatographed simultaneously on a TLC plate in a solvent tank. Semiquantitative and qualitative assessment from all samples is then readily obtained by inspection of the plates, which may be chemically developed and then illuminated to display the separated components (appearing as spots). Further quantitative analysis may be performed using an illumination box, camera, and data acquisition equipment. Unfortunately, conventional TLC apparatus is cumbersome, typically made of glass, and is not field-deployable or field-ruggedized for on-site analysis. Current TLC hardware is not hand portable when including all the necessary support equipment such as plates, tanks, solvent, pipettes, ruler, etc. Furthermore, the illumination and data acquisition equipment needed to fully analyze samples is oversized and extremely heavy. Thus, there is a need for a hand portable, field-ready TLC system, including data acquisition capability, that is cost-effective and efficient for analyzing multiple samples of unknown chemicals on-site in a variety of emergency and non-emergency situations."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a system for analysis of explosives. Samples are spotted on a thin layer chromatography plate. Multi-component explosives standards are spotted on the thin layer chromatography plate. The thin layer chromatography plate is dipped in a hexane, isopropanol, N,N-dimethylformamide, p-xylene, methoxyethanol solvent mixture and chromatography is allowed to proceed. The thin layer chromatography plate is dipped in reagent 1. The thin layer chromatography plate is heated. The thin layer chromatography plate is dipped in reagent 2.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
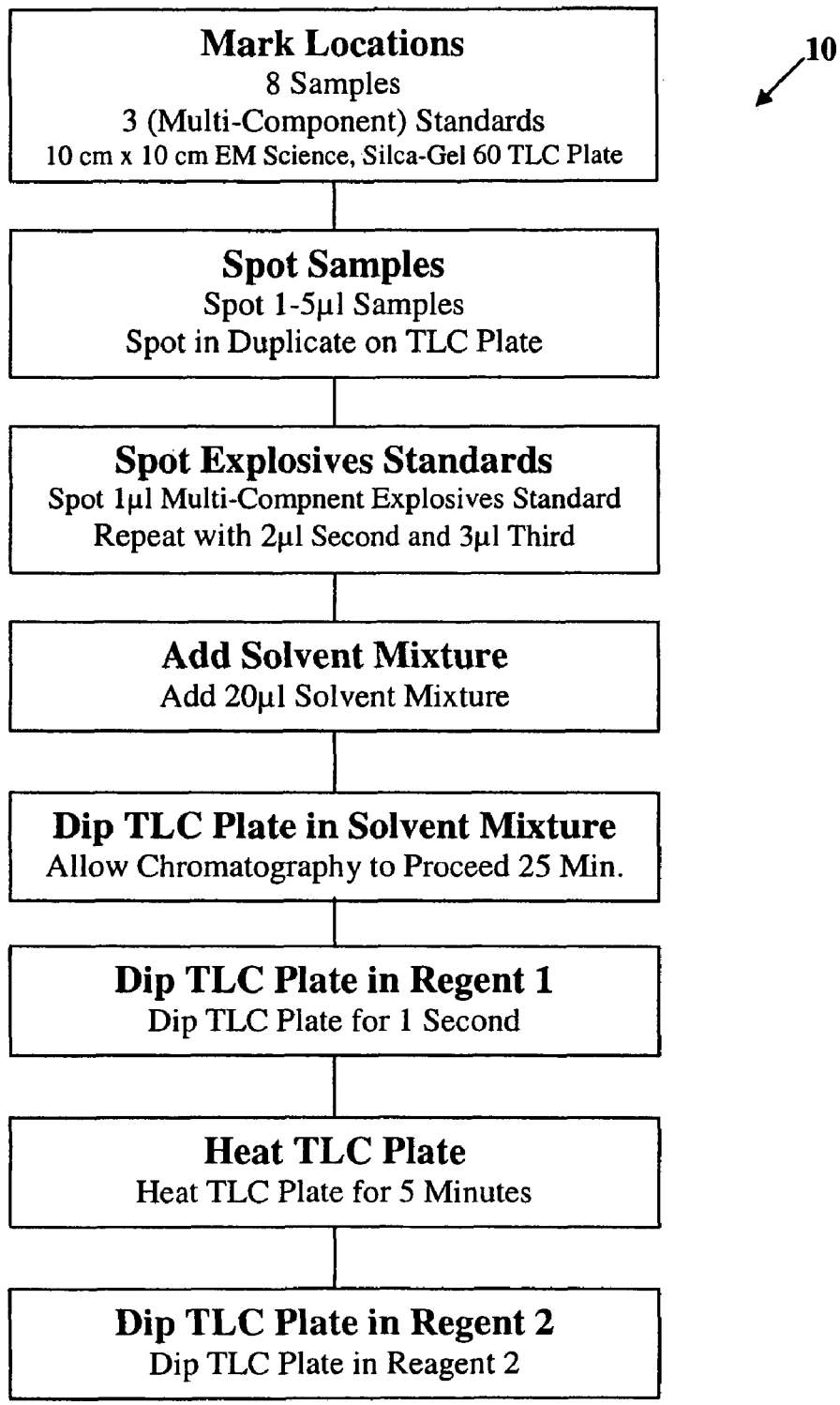
FIG. 1 illustrates a one embodiment of a system for analyzing explosives.

Referring now to the drawings and the following detailed description, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to FIG. 1 of the drawings, an illustration of one embodiment of a system for analysis of explosives constructed in accordance with the present invention is illustrated. This embodiment of a system for analysis of explosives is designated generally by the reference numeral 10.

The system 100 is a Thin-Layer Chromatography (TLC) system. TLC is a technique that is used to judge the purity of a synthesized compound or to indicate the extent of progress of a chemical reaction. In TLC, a small quantity of a solution of the mixture to be analyzed is deposited as a small spot on a TLC plate. A TLC plate consists of a thin layer of silica gel ($SiO_2$) or alumina ($Al_2O_3$) coated on a glass or plastic sheet.

Performing the system for analysis of explosives 10 comprises a number of steps including "Mark Locations," "Spot Samples," "Spot Explosives Standards," "Add Solvent Mixture," "Dip TLC Plate in Solvent Mixture," "Dip TLC Plate in Reagent 1," "Heat TLC Plate," and "Dip TLC Plate in Reagent 2."

The system will now be explained in greater detail. Performing the system for analysis of explosives 10 comprises the steps 11 through 18 shown in FIG. 1. In step 11, 8 Samples and 3 Multi-Component Standards are marked on a 10 cm×10 cm EM Science, Silca-Gel 60 TLC Plate. Step 12 comprises spotting 1-5 µl samples spot in duplicate on the TLC plate. Step 13 comprises spotting a 1 µl multi-component explosives standard on the TLC plate and repeating the spotting with 2 µl second and 3 µl third multi-component explosives standard on the TLC plate. Step 14 comprises adding a 20 ml solvent mixture to the TLC tank. Step 15 comprises dipping the TLC Plate in a solvent mixture and allowing chromatography to proceed for 25 minutes. Step 16 comprises dipping the TLC plate in reagent 1 for 1 second. The reagent 1 provides a Meisenheimer reaction. The Meisenheimer reaction is known in the art and need not be described here. Step 17 comprises heating the TCL plate for 5 minutes. Step 18 comprises dipping the TLC plate in reagent 2. The reagent 2 contains Griess reagent. The Griess reagent is known in the art and need not be described here.

Figure 2:
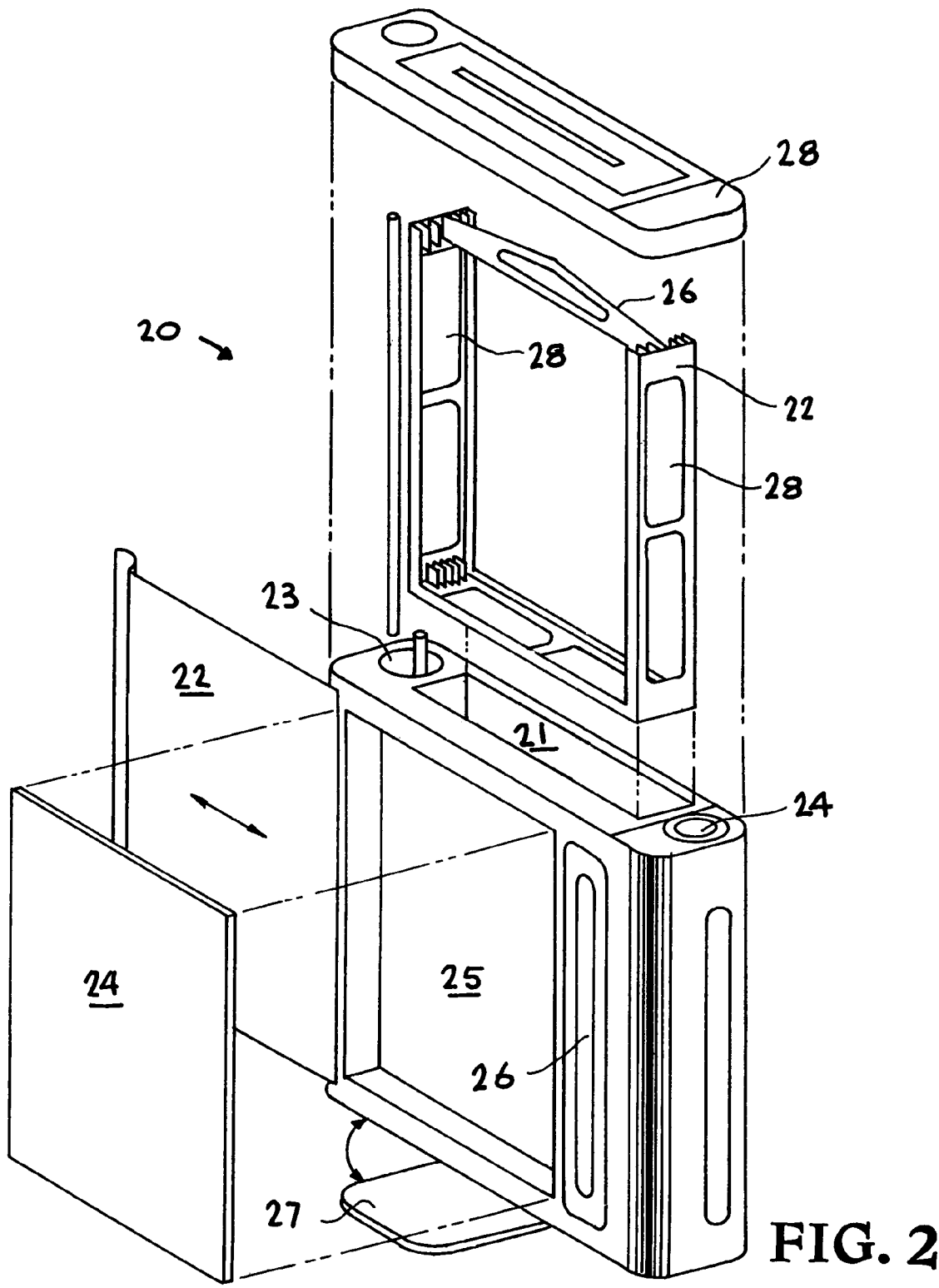
FIG. 2 illustrates one embodiment of a thin layer chromatography apparatus for performing the system for analyzing explosives.

Referring now to FIG. 2, one embodiment of a field-portable thin-layer chromatography (TLC) apparatus for performing the system for analysis of explosives 10 is illustrated. This embodiment of a TLC apparatus is designated generally by the reference numeral 20. The TLC apparatus 20 is suitable for field use. The TLC apparatus 20 fits inside a suitcase and weighs about 23 kilograms. The TLC apparatus 20 can be used to analyze multiple sets of samples simultaneously, with each set containing about a number of samples.

Although The TLC apparatus 20 uses minimal equipment and chemical reagents, it is highly specific and sensitive. The TLC apparatus 20 can be used to analyze two sets of samples simultaneously, with each set containing about 10 samples. Depending on the compounds being analyzed for, the entire process takes 10 to 20 minutes to complete.

The TLC apparatus 20 works by separating compounds over the distance they move up a glass plate. Tiny amounts of samples are placed just above the bottom edge of a TLC plate, the plate is placed in a small solvent reservoir, and the solvent moves up the plate by capillary action. A commercial digital camera captures the resulting patterns of dark spots that develop, which are analyzed on a notebook computer using a software program originally developed for the analysis of DNA. Based on the distance the samples have traveled, together with their color and intensity, the computer program identifies the compounds and their relative position.

The TLC apparatus 20 is tailored to detect chemicals indicative of explosives. The TLC apparatus 20 requires only nanogram to microgram samples, instead of the gram quantities typically required by other methods. The TLC apparatus 20 is also used in instances where analysis speed is essential.

The TLC apparatus 20 contains a solvent tank 21, a holder basket 14 for TLC plates, and a variety of chambers 23, 24, 25 in the frame for storing TLC tools (e.g., pipettes, solvent, TLC plates, ruler). The TLC apparatus 20 may be made of a variety of materials, including stainless steel. The TLC apparatus 20 can be made quite compact, and is only limited by the size of the TLC plates, which are typically 10 cm×10 cm. For example, the dimensions of a portable, field-deployable unit can be about 6 cm.×16 cm.×16 cm.

The small tank reservoir 21 eliminates the need for a saturation pad. A mere 10 ml of solvent can be used to process over 100 samples. The solvent can be stored in a container which fits into one of the storage chambers 18. Pipettes can be stored in another chamber 23. A tool chamber 25 at the front of the unit holds extra TLC plates; in one embodiment, a sliding door 22 that clips in place provides access to the TLC plates 24. The TLC unit has a window 26 for visually monitoring the solvent level during the TLC plate processing.

The holder basket 22 fits into the solvent tank 21, and the basket 22 accommodates a convenient number of TLC plates (e.g., six) for processing. The basket 22 has a unitary body comprising two parallel sides and a bottom portion, is designed to prevent aberrant wicking along the TLC plate edges, which causes the separated components of the multiple samples on the TLC plate to be unevenly distributed across the top of the plate. To prevent this effect, the sides (and bottom) of the basket 22 have openings 28 so that the TLC plates do not touch the sides during processing in the solvent. This design provides superior chromatographic separation of the components. Grooves or separators at the top and bottom of the basket 22 prevent the TLC plates from touching one another. The basket 22 has a handle 26 to facilitate the transfer of the basket 22 in and out of the solvent tank 21.

The TLC apparatus 20 also features a foot (or feet) 27 that swings out from the bottom of the unit to provide additional stability. A lid 28 for covering the unit is gasket-sealed and can be screwed down for better solvent equilibration.

Figure 3:
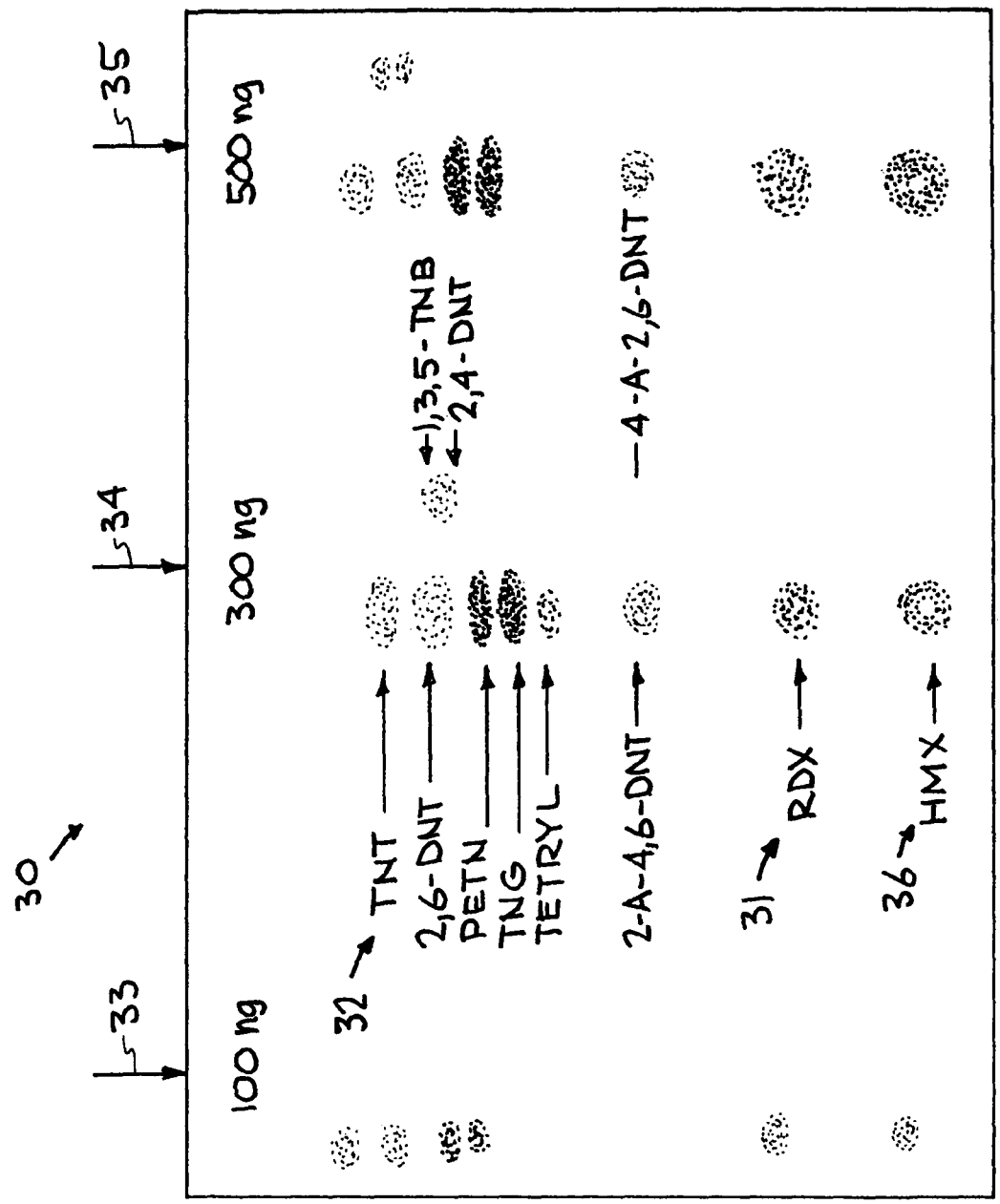
FIG. 3 illustrates one embodiment of a TLC plate used in performing the system for analyzing explosives.

Referring now to FIG. 3, an illustration of one embodiment of a TLC plate used in the present system for analysis of explosives is illustrated. This TLC plate is designated generally by the reference numeral 30. TLC works by separating compounds over the distance they move up the TCL Plate 30. Tiny amounts of samples are placed just above the bottom edge of the TLC Plate 30, the plate 30 is placed in the solvent reservoir 21, and the solvent moves up the plate 30 by capillary action.

A TLC kit that utilizes a digital camera and laptop computer, to identify specific target chemicals is commercially available from Ho'olana Technologies, 212 Holomua Street, Hilo, Hi. 96720. The TLC kit is able to rapidly characterize samples, and can conveniently be used in the field for applications such as environmental clean up, law enforcement investigations, emergency response, and ordinance training. In addition to its portability and rapid analysis ability, Ho'olana Technologies' TLC kit is designed to prevent cross-contamination and promote environmentally sound practices. The unit has an aperture directly above the TLC plate, where the lens of a CCD camera is positioned. The unit and camera are optically aligned for optimum pixel resolution of the CCD images of a standard TLC plate (10 cm×10 cm). The camera may be a commercially available CCD camera (0.25 in CCD, 640×480 pixels) with 24-bit color resolution, where the data are directly recorded onto a 3.5" floppy disk and can be downloaded directly to a computer. Commercially available software may be used to integrate the intensity of each spot, and then analyze the sample by comparison to known compounds.

Performing a TLC analysis consists of a number of steps: preparing a spotting capillary; marking the TLC plate; spotting the TLC plate; developing the TLC plate; drying the plate; visualizing the substance spots, and measuring the $R_f$ values.

In system for analysis of explosives 10 previously described, a small quantity of a solution of the mixture to be analyzed is deposited as a small spot on the TLC plate 30. The TLC plate 30 consists of a thin layer of silica gel ($SiO_2$) or alumina ($Al_2O_3$) coated on a glass or plastic sheet. Samples and multi-component standards are spotted on the TLC Plate 30. The TLC Plate 30 is dipped in a solvent mixture and chromatography is allowed to proceed. The TLC Plate 30 is dipped in reagent 1 for 1 second. The TCL Plate 30 is heated for 5 minutes. The TLC Plate 30 is dipped in reagent 2.

The TLC Plate 30 shown in FIG. 3 is an example of the identification of numerous types of explosives, their concentrations, and the ratio of the amounts of the explosives. The plate 30 shows a mixture of explosives including RXD identified by the reference numeral 31 and TNT identified by the reference numeral 32. The columns 33, 34, and 35 of spots are sets of common explosives one may encounter in a very complex sample. For clarity, only the column of spots 33 is fully labeled.

Each spot of explosive migrates up the TLC Plate 30 away from where it was originally spotted, up to a location on the TLC Plate 30 that is unique for that particular explosive. HMX identified by the reference numeral 36 is the first spot at the bottom. The next one is RDX 31 and so on. The depth of color of the spot is related to its concentration. To show the intensity, each explosive set was spotted at three different concentrations, the lowest on the left and the highest on the right from left to right at 100, 300, and 500 nanograms.

Figure 4:
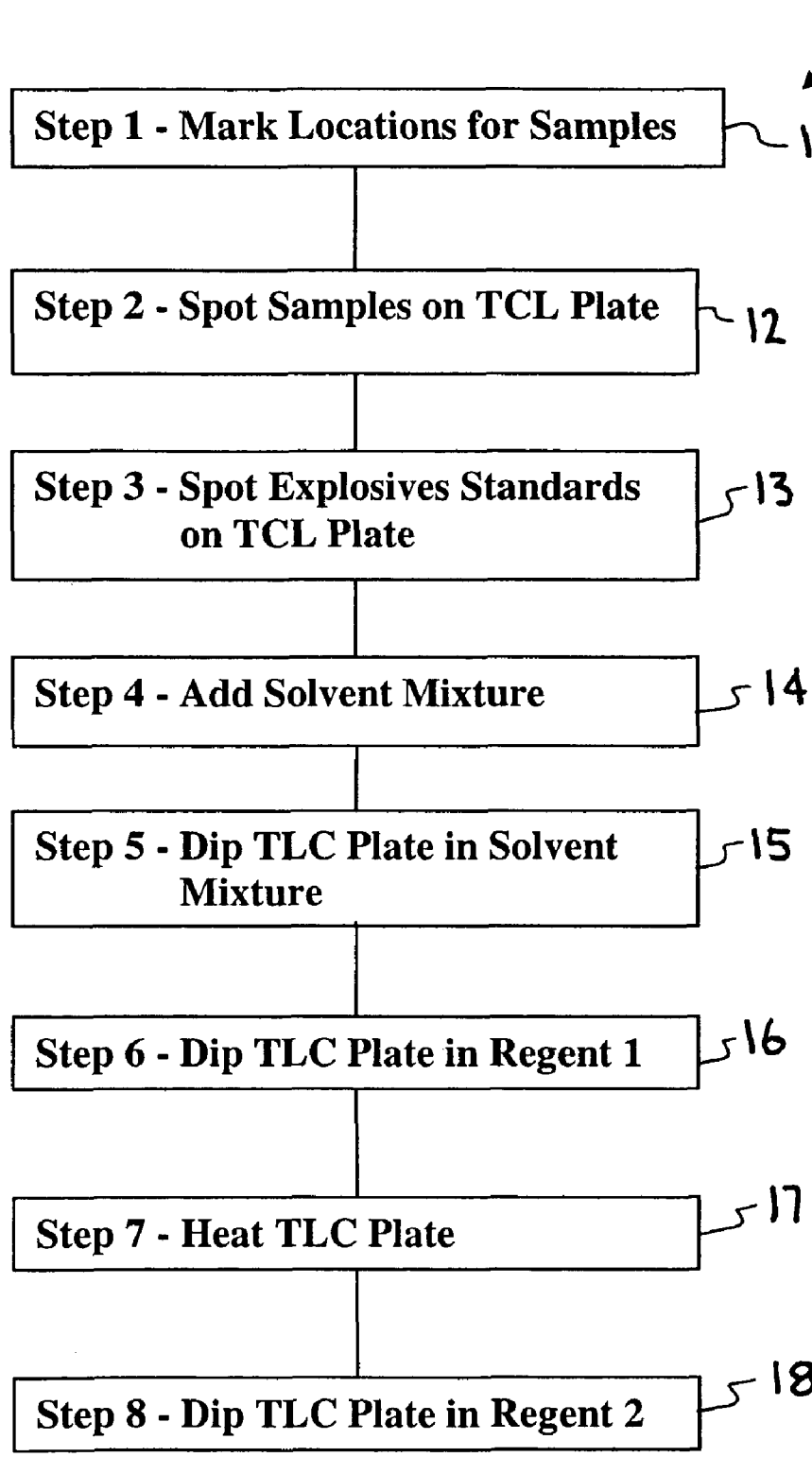
FIG. 4 illustrates another embodiment of a system for analyzing explosives.

Referring now to FIG. 4 of the drawings, an illustration of another embodiment of a system for analysis of explosives constructed in accordance with the present invention is illustrated. This embodiment of a system for analysis of explosives is designated generally by the reference numeral 40. The chemistry concept for elution has been optimized to achieve resolution.

The system for analysis of explosives 40 provides rapid screening capability for the presence of a broad range of explosive residues. The system for analysis of explosives 40 also provides a means for identifying numerous types of explosives, their concentrations, and also provides the capability to ratio the amounts of the explosives present.

The operation of the system for analysis of explosives 40 will now be described. The system for analysis of explosives 40 is performed utilizing a Ho'olana TLC kit commercially available from Ho'olana Technologies, 212 Holomua Street, Hilo, Hi. 96720. Performing the system for analysis of explosives 40 comprises the following steps.

Step 1—Using a pencil, mark locations for 8 samples and 3 (multi-component) standards on a 10 cm×10 cm EM Science, Silica-Gel 60 TLC plate.

Step 2—Spot 1-5 µl of the samples in duplicate, i.e., 4 samples in duplicate on the TLC plate. The TLC plate will therefore, have samples and standards spotted accordingly: 1× standard, sample 1, sample 1 dup., sample 2 sample 2 dup., 2× standard, sample 3, sample 3 dup., sample 4, sample 4 dup., 3× standard at locations 1-11 respectively.

Step 3—Spot 1 µl of a multi-component explosives standard. Repeat the process for the second standard and the third standard with 2 and 3 id, respectively.

Step 4—Add 20 ml of the solvent mixture to the Ho'olana TLC tank in order to perform the chromatography. The solvent mixture is formulated as follows: 80 ml hexane+10 ml isopropanol+3 ml N,N-dimethylformamide+5 ml p-xylene+5 ml of methoxyethanol in the TLC tank.

Step 5—Place the TLC plate in the TLC rack, and then place the rack into the TLC tank containing 20 ml of the solvent mixture. Allow the chromatography to proceed for 25 minutes. Then, pull the rack out of the tank and let the TLC plate dry for a few minutes. TLC plate does not have to be completely dry of solvent before proceeding to the next step.

Step 6—Dip the TLC plate in the Ho'olana Dip tank for one second containing Reagent 1 to get initial colors of explosives. Reagent 1 is formulated as follows: 10 ml of tetrabutylammonium hydroxide 40% in water, Le, 1.5N is added to 90 ml of an iso-propanol/water (50:50) mixture. Then add 0.5 grams of sodium hydroxide to that mixture.

Step 7—Blot off excess Reagent 1 and heat for 5 minutes on the Ho'olana hot plate designed to heat between 100-120° C. More colors, i.e., more explosives will appear.

Step 8—Remove from hot plate and let cool for 30 seconds. Then dip in Reagent 2 which is the Griess reagent.

In summary, the system for analysis of explosives 40 comprises a number of steps including "Step 1-Mark Locations," "Step 2-Spot Samples," "Step 3-Spot Explosives Standards," "Step 4-Add Solvent Mixture," "Step 5-Dip TLC Plate in Solvent Mixture," "Step 6-Dip TLC Plate in Reagent 1," "Step 7-Heat TLC Plate," and "Step 8-Dip TLC Plate in Reagent 2."

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method for analyzing samples for explosives, comprising the steps of:
providing a thin layer chromatography plate,
providing a tank,
providing a solvent mixture,
providing a reagent 1,
providing a reagent 2, and
performing the following combination of steps in the following order:
Step 1, mark locations for the samples on said thin layer chromatography plate,
Step 2, spot samples on said thin layer chromatography plate at said locations,
Step 3, spot multi-component explosives standards on said thin layer chromatography plate at said locations,
Step 4, add said solvent mixture to said tank,
wherein said solvent mixture is formulated as follows: 80 ml hexane+10 ml isopropanol+3 ml N,N-dimethylformamide+5 ml p-xylene+5 ml of methoxyethanol,
Step 5, dip said thin layer chromatography plate in said solvent mixture and allow chromatography to proceed,
Step 6, dip said thin layer chromatography plate in said reagent I and monitor for color to indicate explosives,
Step 7, heat said thin layer chromatography plate, and
Step 8, dip said thin layer chromatography plate in said reagent 2 and monitor for color to indicate explosives.

2. A method for analyzing samples for explosives, comprising the steps of:
providing a thin layer chromatography plate,
providing a tank,
providing a solvent mixture,
providing a reagent 1,
providing a reagent 2, and
performing the following combination of steps in the following order:
Step 1, mark locations for the samples on said thin layer chromatography plate,
Step 2, spot samples on said thin layer chromatography plate at said locations,
Step 3, spot multi-component explosives standards on said thin layer chromatography plate at said locations,
Step 4, add said solvent mixture to said tank, Step 5, dip said thin layer chromatography plate in said solvent mixture and allow chromatography to proceed, Step 6, dip said thin layer chromatography plate in said reagent I and monitor for color to indicate explosives, wherein Step 6 of dipping said thin layer chromatography plate in reagent I comprises dipping said thin layer chromatography plate in reagent I formulated as follows: 10 ml of tetra-butylammonium hydroxide 40% in water, i.e., 1.5N is added to 90 ml of an iso-propanol/water (50:50) mixture, and adding 0.5 grams of sodium hydroxide to that mixture, Step 7, heat said thin layer chromatography plate, and Step 8, dip said thin layer chromatography plate in said reagent 2, and monitor for color to indicate explosives, Step 8, dip said thin layer chromatography plate in said reagent 2 and monitor for color to indicate explosives.

* * * * *